(12) United States Patent
Skinner et al.

(10) Patent No.: US 7,912,270 B2
(45) Date of Patent: Mar. 22, 2011

(54) METHOD AND SYSTEM FOR CREATING AND USING AN IMPACT ATLAS

(75) Inventors: John V. Skinner, New Berlin, WI (US); Gopal B. Avinash, New Berlin, WI (US); Patricia Le Nezet, Le Pecq (FR); Sandeep Dutta, Waukesha, WI (US); Saad Ahmed Sirohey, Pewaukee, WI (US); Deann Marie Haas, Port Washington, WI (US)

(73) Assignee: General Electric Company, Schenectady, NY (US)

( * ) Notice: Subject to any disclaimer, the term of this patent is extended or adjusted under 35 U.S.C. 154(b) by 1156 days.

(21) Appl. No.: 11/602,899

(22) Filed: Nov. 21, 2006

(65) Prior Publication Data

US 2008/0118121 A1 May 22, 2008

(51) Int. Cl.
*G06K 9/00* (2006.01)
(52) U.S. Cl. ....................................... 382/131
(58) Field of Classification Search .................. 600/300, 600/407; 382/100, 128, 129, 130, 131, 132, 382/133, 134, 173, 181; 128/920; 378/1, 378/37, 21, 41, 42, 38, 44, 51, 62, 65, 146
See application file for complete search history.

(56) References Cited

U.S. PATENT DOCUMENTS

| | | | | |
|---|---|---|---|---|
| 5,375,600 A | * | 12/1994 | Melton et al. | 600/455 |
| 5,391,877 A | * | 2/1995 | Marks | 250/363.04 |
| 6,032,120 A | * | 2/2000 | Rock et al. | 705/2 |
| 6,173,068 B1 | * | 1/2001 | Prokoski | 382/115 |
| 6,740,883 B1 | * | 5/2004 | Stodilka et al. | 250/363.04 |
| 7,024,027 B1 | * | 4/2006 | Suri et al. | 382/130 |
| 2003/0053697 A1 | * | 3/2003 | Aylward et al. | 382/203 |
| 2004/0066958 A1 | * | 4/2004 | Chen et al. | 382/128 |
| 2004/0153128 A1 | * | 8/2004 | Suresh et al. | 607/14 |
| 2005/0197547 A1 | * | 9/2005 | Trinks et al. | 600/300 |
| 2005/0234428 A1 | * | 10/2005 | Spohn et al. | 604/533 |
| 2006/0064396 A1 | * | 3/2006 | Wei et al. | 707/1 |

FOREIGN PATENT DOCUMENTS

WO WO 2005/023086 A2 * 3/2005
WO WO 2005/025422 A1 3/2005

OTHER PUBLICATIONS

Faber et al., "Three-Dimensional Fusion of Coronary Arteries with Myocardial Perfusion Distributions: Clinical Validation", Journal of Nuclear Medicine, vol. 45 No. 5 745-753, 2004.*
Lei et al., "Artery-Vein Separation via MRA—An Image Processing Approach", IEEE Transactions on Medical Imaging, vol. 20, No. 8, Aug. 2001, pp. 689-703.*

(Continued)

*Primary Examiner* — Bhavesh M Mehta
*Assistant Examiner* — Tahmina Ansari
(74) *Attorney, Agent, or Firm* — Dean Small; The Small Patent Law Group (57) ABSTRACT

A method and system for processing a cardiac image dataset acquired from an imaging system is provided. A location of a first potential blockage point within a first cardiac vessel is located. A functional impact of the first potential blockage point on the cardiac tissue is predicted, and a representation of the functional impact is provided.

20 Claims, 8 Drawing Sheets

OTHER PUBLICATIONS

Chuang et al., "A Downstream Algorithm Based on Extended Gradient Vector Flow Field for Object Segmentation" IEEE Transactions on Image Processing, vol. 13, No. 10, Oct. 2005, pp. 1379-1392.*

Muhlenbruch et al. Global left ventricular function in cardiac CT. Evaluation of an automated 3D region-growing segmentation algorithm, Journal European Radiology , Publisher Springer Berlin / Heidelberg ISSN 0938-7994 (Print) 1432-1084 (Online), Issue vol. 16, No. 5 May 2006, SpringerLink Date Thursday, Dec. 22, 2005.* myrian® XP Hepatic, Pioneering the automatic detection of hepatic tissues. www.myrian.fr, 2 pgs.

Eric Pichon, Allen Tannenbaum. *Curve Segmentation Using Direectional Information, Relation to Pattern Detection*. Georgia Institute of Technology, 4 pgs.

Eric Pichon, Carl-Fredrik Westin and Allen Tannenbaum. *A Hamilton-Jacobi-Bellman approach to high angular resolution diffusion tractography*. Georgia Institute of Technology, Atlanta GA 30332, USA, 8 pgs.

Kerem Pekkan, et al., Total Cavopulmonary Connection Flow With Functional Left Pulmonary Artery Stenosis: Angioplasty and Fenestration in Vitro, Circulation 2005;112;3264-3271;originally published online Nov. 14, 2005;DOI: 10.1161/CIRCULATIONAHA. 104.530931, http://circ.ahajournals.org/cgi/content/full/112/21/3264.

Matthew D. Ford et al., Virtual Angiography for Visualization and Validation of Computational Models of Aneurysm Hemodynamics, IEEE Transactions on Medical Imaging, vol. 24, No. 12, Dec. 2005.

Foreign Search Report, GE Reference No. 221130 NL, Netherlands S/N: 1034718, filed: Nov. 19, 2007, (12) pages.

* cited by examiner

METHOD AND SYSTEM FOR CREATING AND USING AN IMPACT ATLAS

BACKGROUND OF THE INVENTION

This invention relates generally to processing diagnostic image datasets, and more particularly, to predicting a functional impact of, and evaluating a vulnerability of, an occlusion within a vessel.

Cardiovascular related deaths constitute more than 500,000 people annually in the USA, and much more globally. A major portion of the deaths are attributed to coronary artery disease, where the chief culprit is the build up of plaque, such as soft plaque and its ruptures, as well as hard plaque or calcification.

Typically in x-ray or non-contrasted CT studies, soft plaque is not easily detectable. Calcified plaque, therefore, has been used as a surrogate for the presence of soft plaque, based on the reasoning that calcified plaque is the by-product of ruptured plaque. Coronary plaque has been classified into six stages according to the Stary scale. According to general consensus, it is crucial to determine the plaque in stages 4 and 5 as the plaque constitutes critical vulnerable plaque and could lead to rupture or dislodging of the plaque, causing blockages and leading to myocardial infarction. Plaque and its constituency may be determined by IntraVascular Ultrasound (IVUS). However, the procedure is only performed on symptomatic patients due to its invasive nature. Unfortunately, symptomatic patients are already at an advanced stage and past non-invasive therapy options.

Newer scanning technologies, such as Volume Computed Tomography (VCT), along with associated increases in spatial and temporal resolution, have made it possible to image a contrasted study of the heart which is gated to mitigate heart motion. Using these images, it is possible to distinguish soft plaque from lumen (the vessel wall) and from calcification. However, automated methods do not exist and thus standardization and productivity suffer due to the volume of data to be reviewed and manually processed.

Once a lesion or deposit is identified, a treatment plan may be determined for the patient. No single source exists for providing predictive data based on verified patient case reports, and there is currently no method for automatically predicting the impact of a particular lesion on a particular patient's anatomy. Instead, the extent of the functional impact of an occlusion is typically determined after the occlusion has occurred, such as with a SPECT scan.

Manually analyzing the image datasets is time consuming and prone to error. Also, few care givers have time to spend analyzing substantial amounts of literature to find predictive information corresponding to the specific lesion location of the patient. As a result, the recommendations for care may be influenced by a variety of other factors, such as experience of the care giver, case load, availability of equipment, reimbursement for care, and the like. This may lead to inconsistencies and missed opportunities for utilizing non-invasive therapy options.

Therefore, a need exists for evaluating potential occlusions within a vessel to determine potential functional impact. Certain embodiments of the present invention are intended to meet these needs and other objectives that will become apparent from the description and drawings set forth below.

BRIEF DESCRIPTION OF THE INVENTION

In one embodiment, a method for processing a cardiac image dataset acquired from an imaging system comprises identifying a location of a first potential blockage point within a first cardiac vessel. A functional impact of the first potential blockage point on the cardiac tissue is predicted, and a representation of the functional impact is provided.

In another embodiment, a method for creating an impact atlas for predicting impact of a blockage within a vessel comprises identifying potential blockage points within cardiac vessels of an image dataset. Impact regions are grown based on the blockage points within the cardiac vessels. Each of the blockage points are associated with at least one of the impact regions in an impact atlas file.

In another embodiment, a system for displaying potential impact of an occlusion within a coronary vessel comprises a display, a user interface and a processor coupled to the display and user interface. The display displays an image dataset comprising at least anatomical structures indicative of cardiac vessels and a list of anatomical points identifying locations within the cardiac vessels. Each of the anatomical points has at least one associated potential impact region defining an area of decreased blood flow based on an occlusion located proximate to the anatomical point. A first anatomical point is selected from the list using the user interface. The first anatomical point is based on a first potential occlusion point. The processor identifies data associated with the first anatomical point, and the display displays the data representative of the potential impact region associated with the first anatomical point.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Although a computed tomography (CT) imaging system 10 is discussed for reference below, it should be understood that other non-invasive diagnostic imaging modalities may be used to generate a three dimension (3D) image dataset, such as PET, MRI, interventional X-ray and ultrasound. Also, the examples below refer primarily to cardiac conditions, but the techniques may be equally applied to other organs and systems within the body. The techniques may further be applied to other detectable networks within the body, such as structures which transmit air in the lung, for example.

Figure 1:
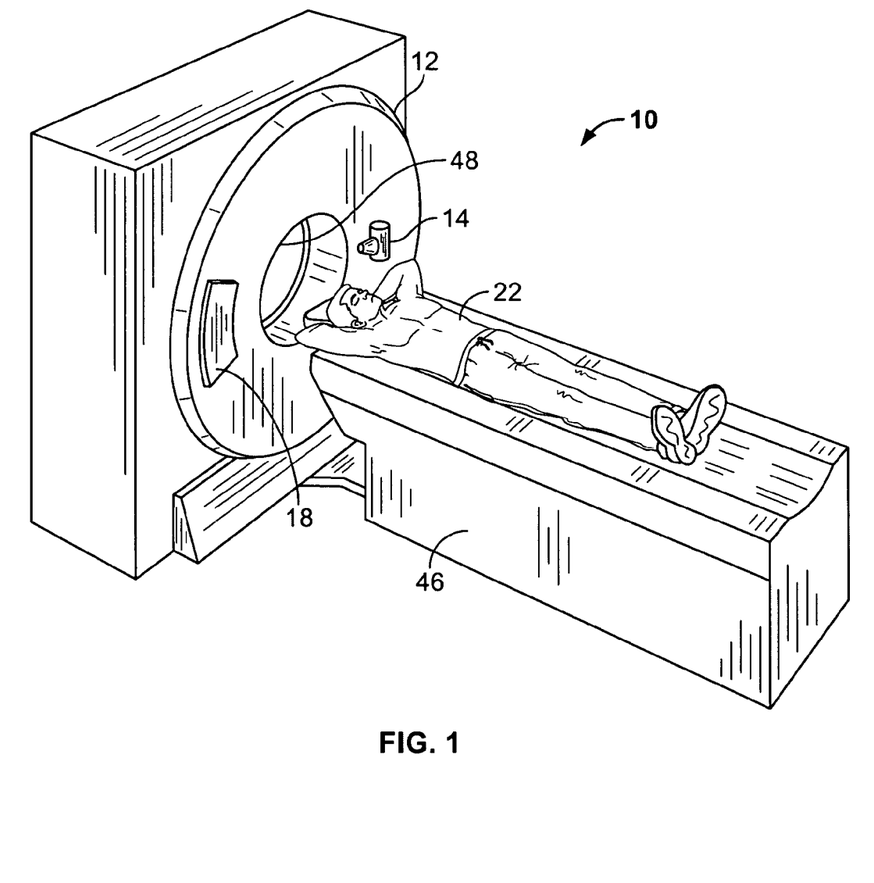
FIG. 1 illustrates a pictorial view of a computed tomography (CT) imaging system in accordance with an embodiment of the present invention.
Figure 2:
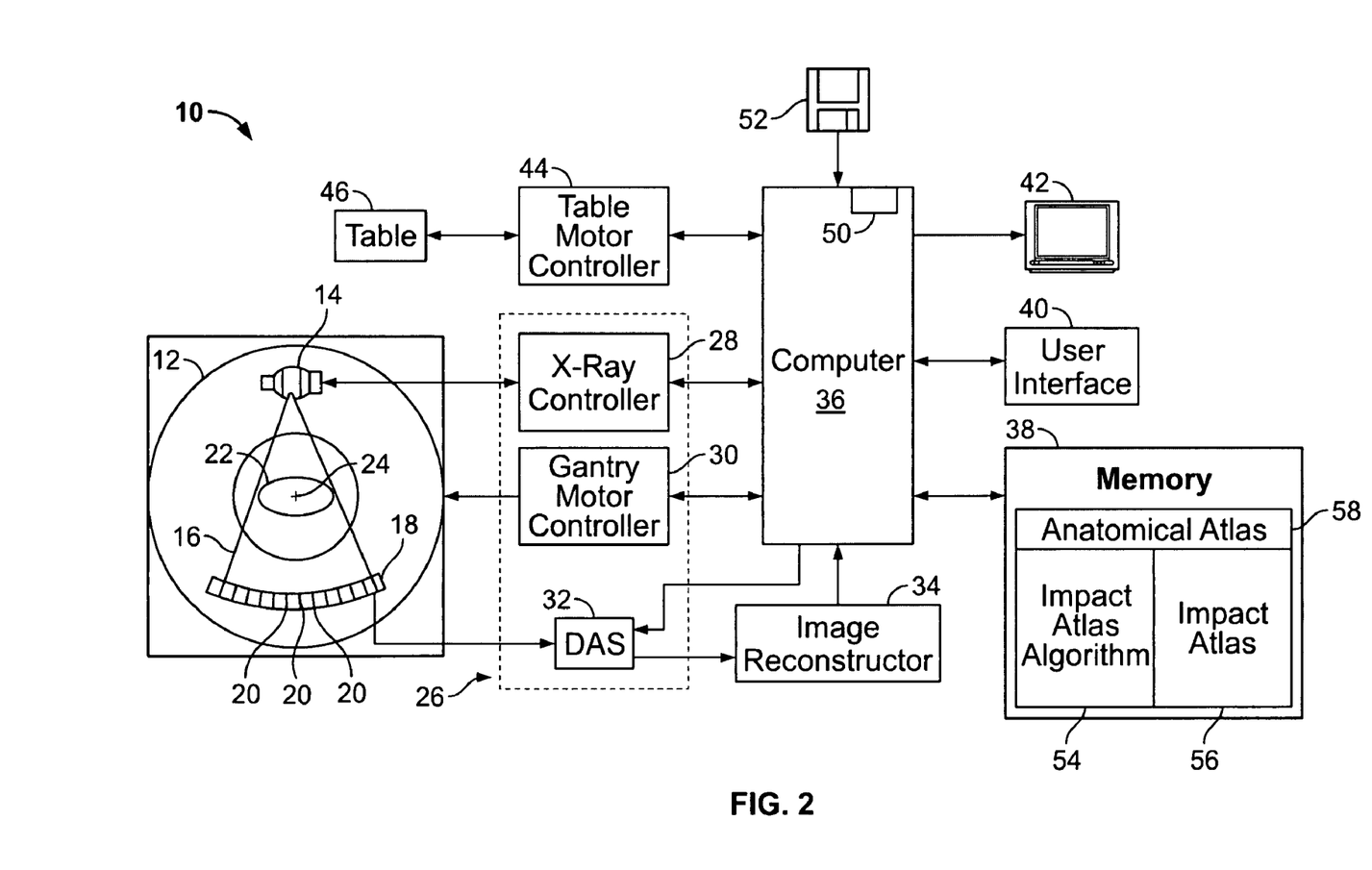
FIG. 2 illustrates a block diagram of the system of FIG. 1 in accordance with an embodiment of the present invention.

FIG. 1 illustrates a pictorial view of a computed tomography (CT) imaging system 10. The system 10 includes a gantry 12 representative of a "third generation" CT imaging system. FIG. 2 illustrates a block diagram of the system 10 of FIG. 1, and will be discussed together with FIG. 1.

The gantry 12 has an x-ray source 14 that projects a beam of x-rays 16 toward a detector array 18 on the opposite side of the gantry 12. The detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through the patient 22. During a scan to acquire x-ray projection data, the gantry 12 and the components mounted thereon rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of the gantry 12 and the operation of the x-ray source 14 are governed by a control mechanism 26 of the CT system 10. The control mechanism 26 includes an x-ray controller 28 that provides power and timing signals to the x-ray source 14 and a gantry motor controller 30 that controls the rotational speed and position of the gantry 12. A data acquisition system (DAS) 32 in the control mechanism 26 samples analog data from the detector elements 20 and converts the data to digital signals for subsequent processing. An image reconstructor 34 receives sampled and digitized x-ray data from the DAS 32 and performs high-speed image reconstruction. The reconstructed image is applied as an input to a computer 36 which stores the image dataset in memory 38.

The computer 36 also receives commands and scanning parameters from an operator via user interface 40 that has input devices such as a keyboard, mouse, trackball and the like. An associated display 42 allows the operator to observe the reconstructed image and other data from the computer 36. Optionally, operator input may be provided through a touch screen monitor. The operator supplied commands and parameters are used by the computer 36 to provide control signals and information to the DAS 32, x-ray controller 28, and gantry motor controller 30. In addition, the computer 36 operates a table motor controller 44 which controls a motorized table 46 to position the patient 22 with respect to the gantry 12. Particularly, the table 46 moves portions of the patient 22 through gantry opening 48.

In one embodiment, the computer 36 includes a device 50, for example, a floppy disk drive or CD-ROM drive, for reading instructions and/or data from a computer-readable medium 52, such as a floppy disk or CD-ROM. In another embodiment, the computer 36 executes instructions stored in firmware (not shown). The computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Also, it should be understood that the computer 36, display 42 and user interface 40 may be provided separate from the system 10 for processing data. The acquired image datasets may be transferred over a network, internet, by portable disk, and the like, for processing at a location remote from the system 10, such as on a separate workstation, computer, PACS review station and the like.

Currently, anatomical atlases of various organs are available, providing a standardized way of representing information. For example, a cardiac anatomical atlas 58 of the heart may be stored in the memory 38 and used to identify landmarks within a patient's cardiac image dataset. The anatomical atlas 58 may be based primarily on known historical cases. Although helpful, the anatomical atlas 58 does not provide functional data with respect to the heart, and thus the impact of a blockage within a vessel is not known until the blockage has occurred and subsequent diagnostic testing is accomplished to identify impacted areas.

A cardiac impact atlas 56 as discussed below may be accessed to provide functional impact data prior to a blockage occurring. The impact atlas 56 may be stored in the memory 38 as a database or other file format, and may access information within the anatomical atlas 58 and/or incorporate the anatomical atlas 58 therein. The impact atlas 56 provides predictive data to help predict the impact of dislocation of a deposit on cardiac function, determine whether a plaque deposit is vulnerable to dislocation, as well as assist with the identification of anomalies within the cardiac coronary artery system.

An impact atlas algorithm 54 is also stored in the memory 38. The impact atlas algorithm 54 may facilitate creating an impact atlas to be used by multiple patients, creating an impact atlas specific to a patient's unique image dataset, adding predictive functionality to the anatomical atlas 58, as well as combinations thereof. In addition, the impact atlas algorithm 54 facilitates collection of data over time which may be incorporated into the impact atlas 56 to improve the sophistication and predictive abilities.

Figure 3:
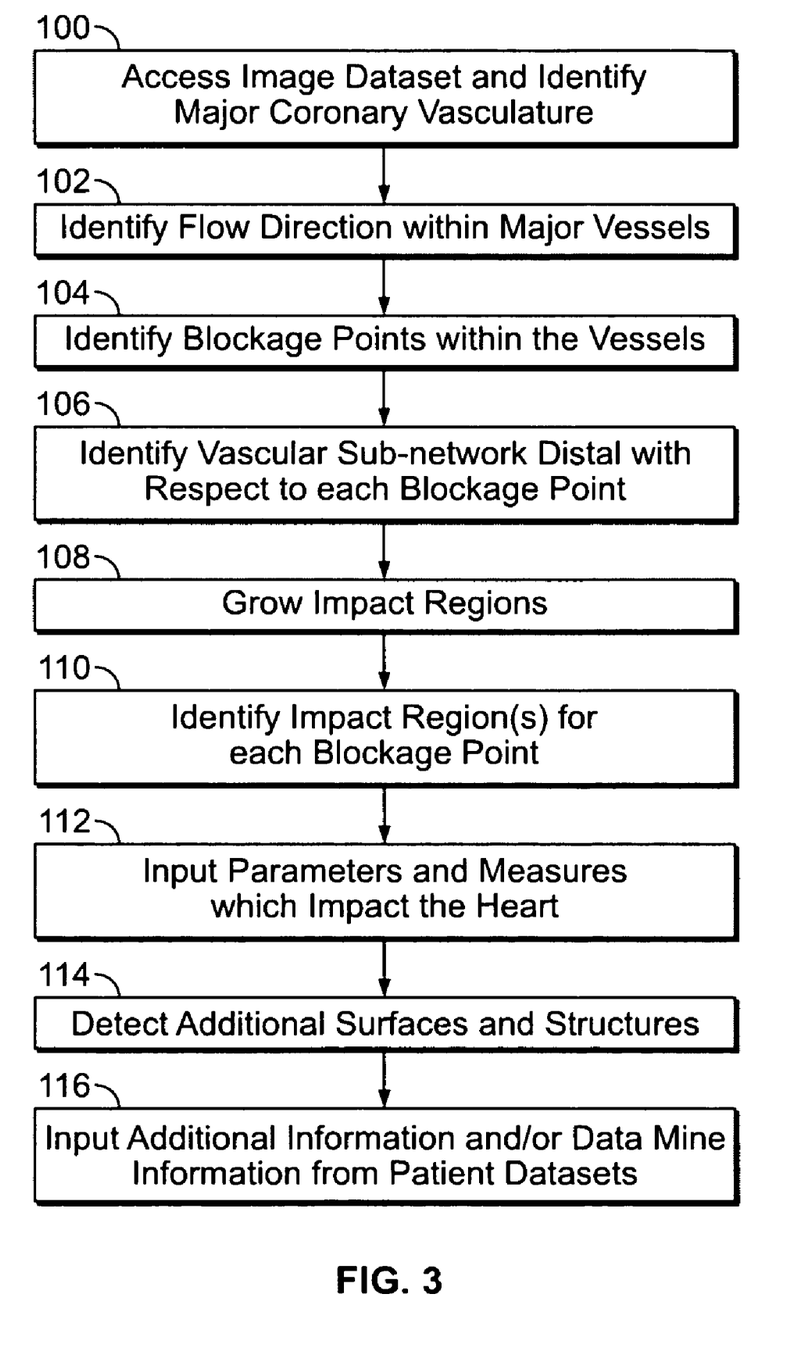
FIG. 3 illustrates a method for creating an impact atlas that may be used to predict functional impact regions of a blockage within a vessel in accordance with an embodiment of the present invention.

FIG. 3 illustrates a method for creating an impact atlas that may be used to predict functional impact regions of a blockage within a vessel. The method provides an algorithmic way to predict a result, which may be further improved upon by the addition of other functional organ data and/or data based on a particular patient or groups of patients. The impact atlas may also eliminate the need for other functional studies which are expensive and time consuming. The heart is used in this example, however, it should be understood that an impact atlas may be created for other organs, systems, and structures within the body. The impact atlas may be created substantially automatically by the impact atlas algorithm 54 with a minimum number of user inputs. Alternatively, the impact atlas may be created based on a number of user inputs. Multiple impact atlases may be established for different patient profiles, such as patient age, weight, sex, or representative of a structural defect.

At 100, the impact atlas algorithm 54 accesses an image dataset which may be representative of a desired patient profile. For example, the computer 36 may identify major coronary vasculature, which includes at least the left coronary artery, right coronary artery, pulmonary arteries and aorta using segmentation or other feature extraction algorithms. Alternatively, the impact atlas algorithm 54 may access the pre-existing anatomical atlas 58 which may be based on a large number of datasets that have the anatomical structures with correspondence points identified and labeled.

At 102, the impact atlas algorithm 54 identifies a flow direction within each major vessel. This may be data which is known or determined based on known anatomical function for each major vessel, or may be stored within the anatomical atlas 58. Alternatively, a user may identify a general flow direction within each major vessel with the user interface 40. The user may also be able to confirm and/or change an automatically detected flow direction.

Figure 4:
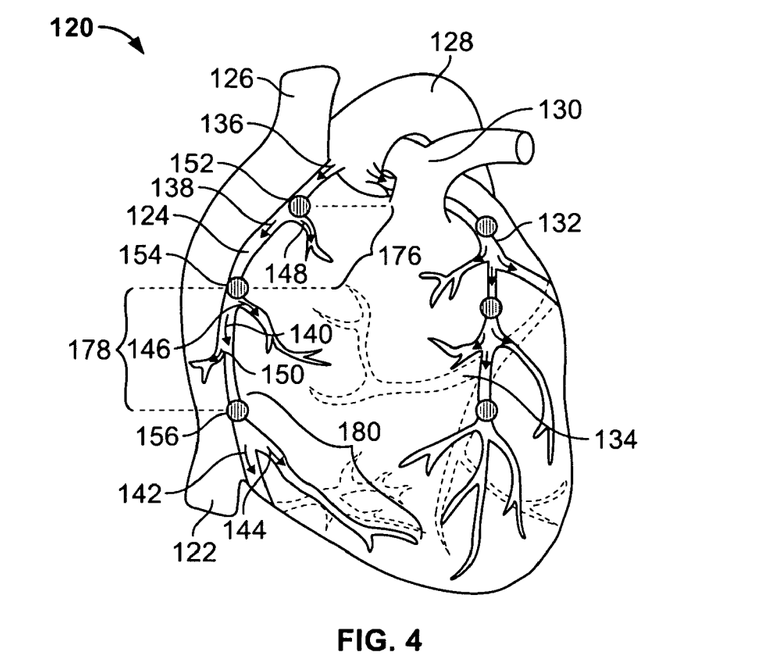
FIG. 4 illustrates a visual representation of the impact atlas which may be displayed to the user on a display in accordance with an embodiment of the present invention.

FIG. 4 illustrates a visual representation 120 of the impact atlas 56 which may be displayed to the user on the display 42. At least a portion of the major coronary vasculature is illustrated, including inferior vena cava 122, right coronary artery 124, superior vena cava 126, aorta 128, pulmonary arteries 130, left coronary artery 132, and circumflex branch of the left coronary artery 134. Arrows 136-150 indicate the general direction of blood flow through portions of the right coronary artery 124 and vessel branches. Arrows (without item numbers) are also used to indicate the general direction of blood flow though portions of the left coronary artery 132.

At 104 of FIG. 3, the impact atlas algorithm 54 identifies blockage points or lesions within the major vessels. The blockage points are positioned along the length or extent of a vessel and its branches, and divide the major vessels into multiple segments. The blockage points and segments define the 3D axis which will volumetrically grow to describe the tissue impact regions associated with a blockage at the proximal or input blood flow point of the vessel. For example, it may be advantageous to identify a blockage lesion just upstream of each vessel branching point, as an occlusion located prior to the branching point would affect all tissue fed by the branching vessels. Optionally, a single initial blockage point may be identified automatically at a input point of a vessel as derived from anatomical landmarks, such as at the points where the right coronary artery 124 and left coronary artery 132 branch from the aorta 128, or by the user through the user interface 40.

In FIG. 4, blockage points 152-156 are indicated within the right coronary artery. The blockage points 152-156 represent potential vessel occlusion points upon which 3D impact regions are at least partially based. The 3D impact regions identify potentially compromised tissue.

At 106 of FIG. 3, the impact atlas algorithm 54 identifies a vascular sub-network distal or downstream from each of the blockage points 152-156. The impact atlas algorithm 54 moves in the direction of blood flow, identifying first, second and third vascular sub-networks associated with blockage points 152, 154 and 156, respectively. Any tissue fed by the vessel downstream of the blockage point 152-156 would be impacted by an occlusion located proximate to the blockage point 152-156. Each point in the vascular sub-network distal to a blockage point is assigned a unique identifier, which will also be used to identify tissue within the associated impact regions as discussed below.

At 108, the impact atlas algorithm 54 grows impact regions based on the blockage points 152-156 to determine the nearest volumetric regions that may be potentially affected by the vessel occlusion. The impact regions are estimated based on proximity to the vessels providing blood supply. When growing the impact regions, the vascular sub-networks defined between two blockage points are treated as a separate vessel. Although only one vessel is discussed, it should be understood that there may be many more blockage points identified and that the impact atlas algorithm 54 may grow the associated impact regions singularly or simultaneously. Alternatively, in one embodiment, a single blockage point is identified and the impact region is detected on-the-fly. This embodiment is discussed below in FIG. 9.

In one embodiment, all points within the image representative of tissue may be assigned the same identifier, such as zero. Each impact region will be assigned a different or unique identifier. The impact atlas algorithm 54 simultaneously grows the impact regions associated with each of the first, second and third vascular sub-networks 176-180. Starting from vessel points along each of the sub-networks, each vessel point grows by one layer in three dimensions, and area incorporated into each particular impact region is identified by the unique identifier. The impact atlas algorithm 54 stops growing an impact region when a boundary of a different impact region is reached, indicated with a different identifier, an end of the volume is reached, or structure excluded from the algorithm is encountered. This provides the estimated boundaries of the blood supply contributions.

In another embodiment, boundaries may be established within the segmented tissue based on the blockage points. The impact atlas algorithm 54 grows the impact regions as a propagation wave front starting with the blockage point. The impact region is grown distally with respect to the blockage point until a boundary of a different impact region is reached or a next blockage point is detected. Optionally, the impact region may be grown anti-distally with respect to the blockage point. The growth in the anti-distal direction or upstream of the blockage point may be at a slower rate than the growth of the impact region downstream of the blockage point.

Optionally, the amount of growth for a particular vessel point may be determined based on the size of the vessel. This may take into consideration that a larger vessel provides a larger blood supply and thus has a greater impact on surrounding tissue. For example, a larger vessel may grow layers twice as quickly as a smaller vessel.

Figure 5:
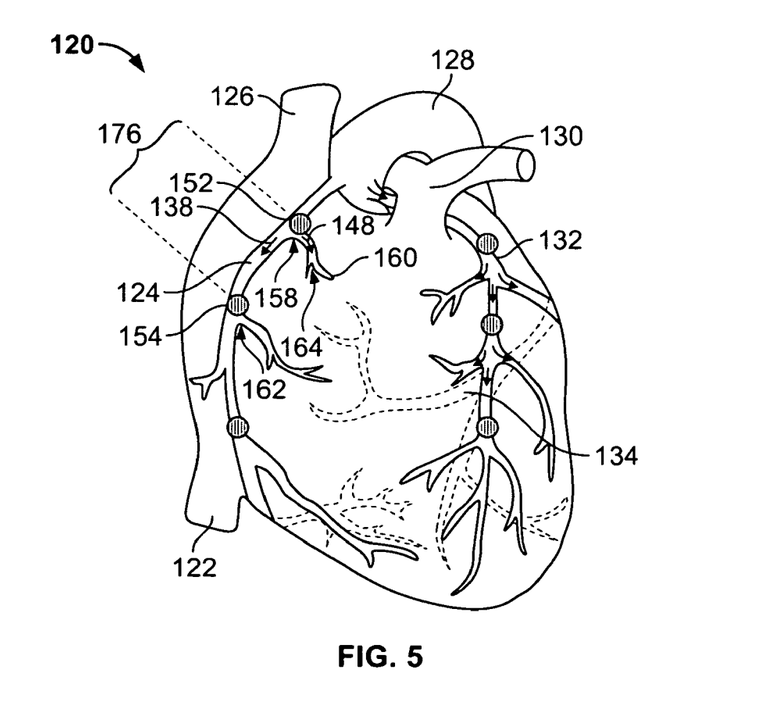
FIG. 5 illustrates region growing from blockage points within the right coronary artery on the visual representation of the impact atlas in accordance with an embodiment of the present invention.

FIG. 5 illustrates region growing from blockage points within the right coronary artery 124 on the visual representation 120 of the impact atlas 56. This process provides a method for dividing up regions of the heart into impact regions which may be easily indexed or otherwise correlating potential tissue damage to locations of occlusions. A single blockage point is discussed. The impact atlas algorithm 54 may start at the blockage point 152, which has been located prior to vessel branching point 158. The impact atlas algorithm 54 identifies the first vascular sub-network 176, moving in the directions of arrows 138 and 148. The impact atlas algorithm 54 may grow an impact region by growing points along the first vascular sub-network 176, such as until a boundary of an impact region associated with the blockage point 154 is detected, when the blockage point 154 is detected, or when the end of the tissue volume is detected, as discussed previously. Alternatively, the impact region may be grown from the blockage point 152, propagating as a wave front along the first vascular sub-network 176 and into surrounding tissue. Also, the impact atlas algorithm 54 may operate on all vascular sub-networks and/or blockage points at the same time.

Figure 6:
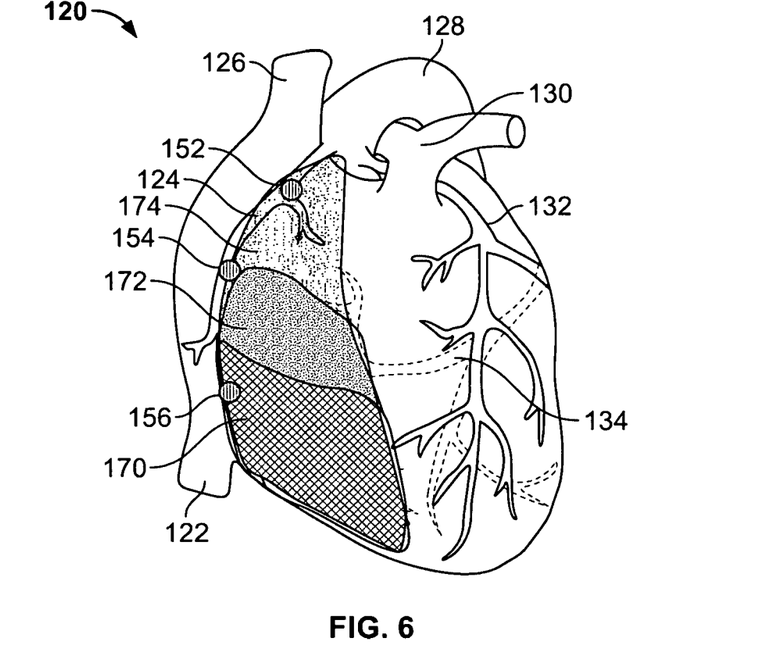
FIG. 6 illustrates the visual representation of the impact atlas having impact regions displayed thereon in accordance with an embodiment of the present invention.

At 110 of FIG. 3, the impact atlas algorithm 54 identifies one or more impact regions associated with each blockage point 152-156. FIG. 6 illustrates the visual representation 120 of the impact atlas 56 having impact regions displayed thereon. The blockage point 156 is associated with first impact region 170. The first impact region 170 extends downstream from the blockage point 156 and into surrounding tissue. The first impact region 170 also extends upstream or distal to the blockage point 156.

The blockage point 154 is associated with second impact region 172 as well as the first impact region 170 because the first impact region 170 is downstream from the blockage point 154. The blockage point 152 is associated with third impact region 174 as well as the first and second impact regions 170 and 172. Although the impact regions 170-174 are illustrated in substantially two dimensions in FIG. 6, it should be understood that the impact regions are defined in three dimensions and thus may be displayed on the display 42 in 3D.

At 112 of FIG. 3, the user may input parameters and measures which impact the heart with the user interface 40. Parameters may be physiological measures such as ejection fraction and stroke volume, as well as typical blood flow and vessel movement due to cardiac function. Also, an impact value may be determined for each vessel or sub-network of a vessel based on location. Therefore, the impact atlas 56 may have a cross-referenced list or database including each vessel and at least one associated impact value.

At 114, the impact atlas algorithm 54 may detect additional surfaces and structures within the heart, if not previously detected at 100 along with the coronary vasculature. Segmentation or other surface detection algorithms may be used to determine surfaces of the ventricles, general pathways along the surface of the vessels, as well as valves. These structures provide additional data which may be displayed together with the vessels.

At 116, the user may enter additional data with the user interface 40 regarding the functionality of the heart. The data may be used by the impact atlas algorithm 54 when detecting impact regions or determining the level of vulnerability of a blockage. This data may be known to the user based on personal experience or case studies, for example. In addition, as the impact atlas 56 is used with patient datasets, the impact atlas algorithm 54 may data mine information regarding structures and properties which may be included within the database of the impact atlas 56 to improve its predictive capabilities. Optionally, the impact regions may be determined and/or verified and/or modified by classic patient cases which have been verified. Therefore, historical cases may be used to create and/or supplement the impact atlas 56.

The impact atlas 56 may be used to display and predict impact of disease with or without cross-reference to a patient's dataset. The impact atlas 56 may be used as a training or teaching tool, as well as to help a patient understand their disease as well as treatment options. The impact atlas 56 may be displayed, and by selecting one or more blockage points along vessel(s), the potential impact region(s) are determined and displayed.

Figure 7:
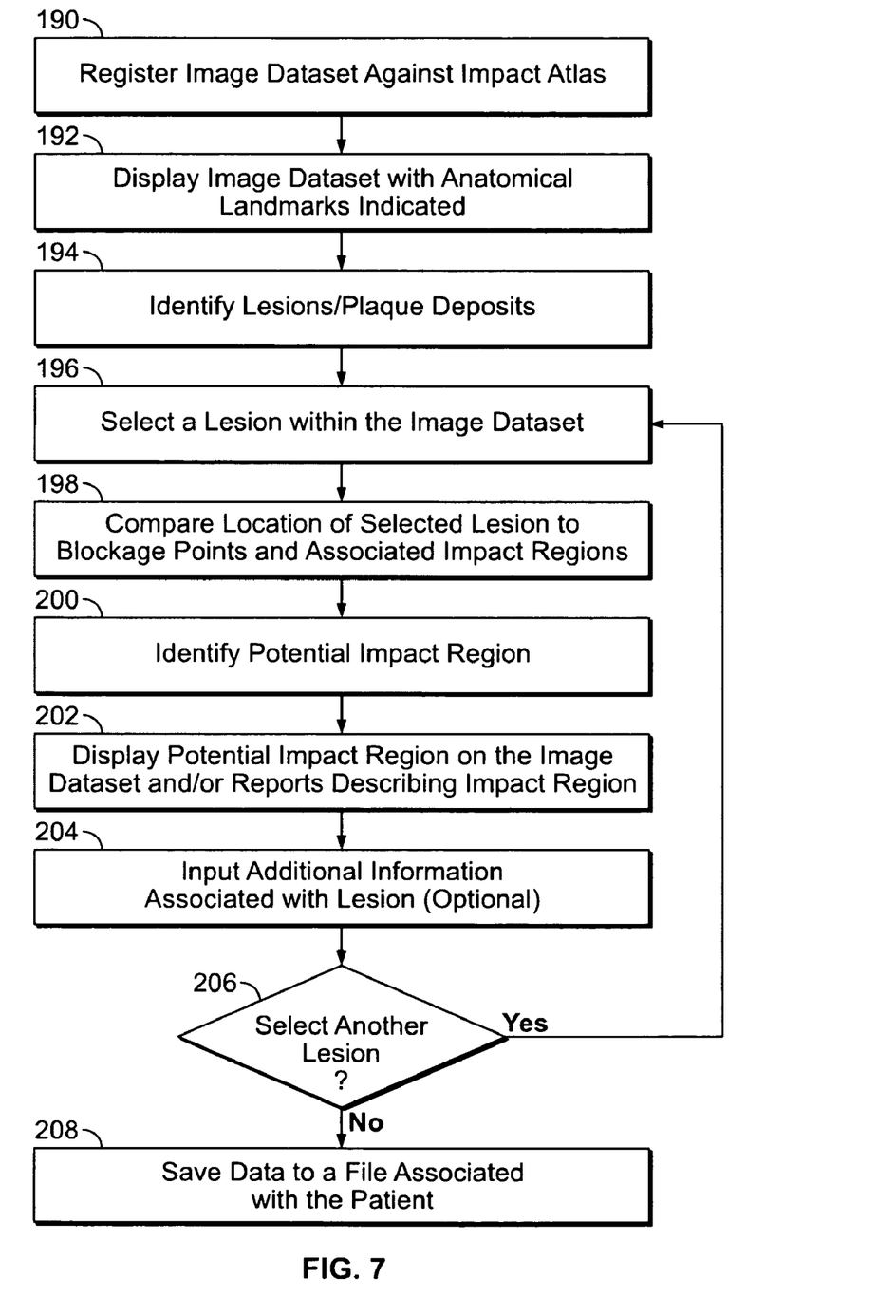
FIG. 7 illustrates a method for using the impact atlas of FIG. 3 to predict impact of a potential occlusion or blockage within the heart represented by a patient's cardiac image dataset in accordance with an embodiment of the present invention.

FIG. 7 illustrates a method for using the impact atlas 56 created in FIG. 3 to predict impact of a potential occlusion or blockage within the heart represented by a patient's cardiac image dataset. At 190, the impact atlas algorithm 54 registers a segmented image dataset against the impact atlas 56 to correlate the anatomical landmarks stored within the impact atlas 56 to the structures within the image dataset. For example, anatomical landmarks, automatically detected or indicated by the user, of the general location of the coronary arteries in the patient, are used to register the patient's 3D image dataset against the impact atlas 56. At 192, the impact atlas algorithm 54 displays the image dataset with the anatomical landmarks indicated on the display 42. The registering and display of the patient dataset may also help identify anomalies present within the patient's coronary artery system.

At 194, the user may then interact with the display 42 to view desired portions and/or views of the image dataset. The user reviews the image dataset to identify soft and hard plaque deposits within the vessels, as well as any other anomalies of interest. Some amount of plaque deposit may be considered normal, but beyond a particular size or percentage of occlusion, the plaque deposit may be identified as vulnerable to dislocation and/or requiring treatment. If a soft plaque deposit is present which is of a predetermined size or greater, it may be vulnerable to rupture and may form hard plaque or calcification. A plaque deposit which becomes dislocated may cause an occlusion at the present location or downstream within the vessel.

Optionally, the image dataset may be processed automatically to identify plaque deposits of interest. Optionally, the impact atlas algorithm 54 may calculate a vulnerability score for the selected or detected plaque deposits. Due to heart wall motion, blood flow volume and velocity, composition of plaque, as well as other factors, a plaque deposit at a first location may be determined to be more vulnerable than a plaque deposit at a second location. The locations of the vulnerable plaque deposits may then be automatically indicated on the display 42 with the image dataset and the anatomical landmarks for further review by the user.

Figure 8:
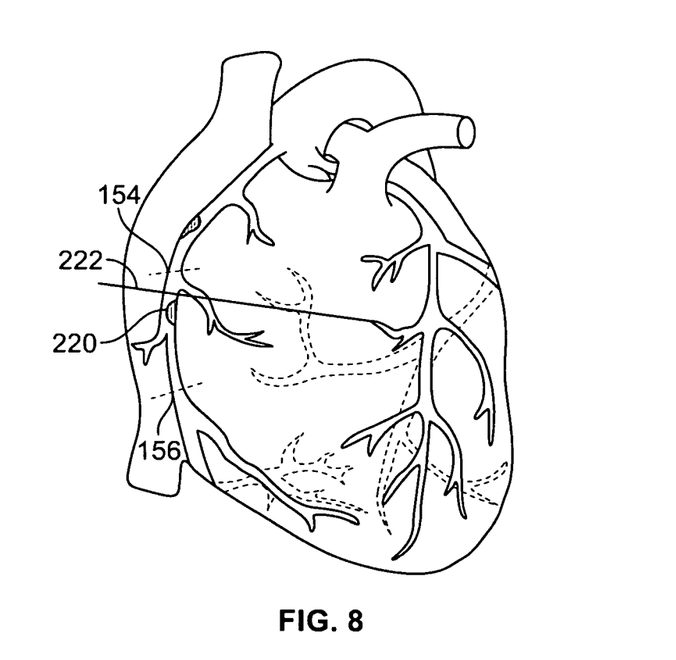
FIG. 8 illustrates the image dataset displayed on the display with a lesion indicated in accordance with an embodiment of the present invention.

At 196, the user selects a lesion with the user interface 40. The lesion may be located anywhere within a vessel. FIG. 8 illustrates the image dataset displayed on the display 42 with lesion 220 indicated. At 198 of FIG. 3, the impact atlas algorithm 54 compares a location of the lesion 220 to locations of blockage points 152-156 as well as the first through third impact regions. The impact atlas algorithm 54 may identify both the blockage point 154, which is upstream from the lesion 220 and the blockage point 156, which is downstream from the lesion. The locations of the blockage points 154 and 156 are indicated using dashed lines on FIG. 8.

At 200, the impact atlas algorithm 54 identifies a potential impact region for the lesion 220 based on the blockage points 154 and 156 and their respective impact regions 170 and 172 (FIG. 6). The impact atlas algorithm 54 may consider several factors when identifying the potential impact region. For example, if the lesion 220 is located near the upstream blockage point (blockage point 154), the impact region associated with the upstream blockage point may be included in the potential impact region. Optionally, only a portion of the impact region associated with the upstream blockage point which is located distal of the lesion 220 may be included. For example, a plane 222 may be formed upstream of the lesion 220, excluding areas of the second impact region 172 (FIG. 6) above the plane 222. Optionally, if the lesion 220 is identified immediately upstream of the downstream blockage point (blockage point 156), the impact region associated with the upstream blockage point (second impact region 172) may be ignored, and only the region(s) associated with the downstream blockage point (blockage point 156) are used to form the potential impact region. Optionally, the impact atlas algorithm 54 may include the potential impact regions associated with the upstream and the downstream blockage points, and indicate the portion above the plane 222 with a different indication to identify tissue area which may experience little or no impact from the lesion 220.

At 202 of FIG. 7, the impact atlas algorithm 54 displays the potential impact region on the display 42 with the anatomical data and impact atlas data. Optionally, the impact atlas algorithm 54 may display the potential impact region as data within a report or with other written descriptors, such as textual reports and/or summaries, or may visually display the potential impact region on a separate heart model. Optionally, a comparison of the patient's image dataset with the impact atlas 56 may be displayed. For example, various displays may be used, such as 3D surface rending of an atlas model, 3D volume render fusion marking actual impact regions, highlighting the impact regions on Polar Plot diagrams, and 2D plots.

Referring again to FIG. 6, if the blockage point 156 was identified as the lesion at 196 (FIG. 7), the first impact region 170 would be indicated on the display 42. The indication may be accomplished by changing a color within the first impact region 170, hash marks, varied gray scale, flashing, or any other indication which distinguishes the potential impact region from the surrounding tissue. The user may rotate, pan and zoom the images on the display 42 as desired.

At 204 of FIG. 7, the user may optionally input additional information associated with the lesion 220 with the user interface 40. Additional information may be a peak height, volume, and/or composition of the deposit. The user may also input a percentage of blockage or occlusion. The impact atlas algorithm 54 may adjust the impact region based on this information. For example, a greater percentage of blockage would generally result in a higher level of impact.

At 206, if the user wants to select a subsequent lesion, the method returns to 196. The user may determine whether all, some or none of any previously identified impact regions are to be displayed concurrently with a most recently identified impact region. For example, the user may toggle the previously detected impact regions on and off with the user interface 40. Alternatively, at 202 the impact atlas algorithm 54 may display each impact region differently, as well as uniquely indicating areas of overlap between impact regions, to assist the user in identifying the impact of each of the lesions.

If no lesion is selected at 206, at 208 the impact atlas algorithm 54 saves the data to a file. The file may be a database, image file, and/or other file stored within the memory 38 and associated with the patient diagnostic data. The stored data may be accessed in the future to review and/or print results and images, as well as compare previously detected lesions with currently detected lesions and their associated impact regions to track progression of disease within the patient.

Figure 9:
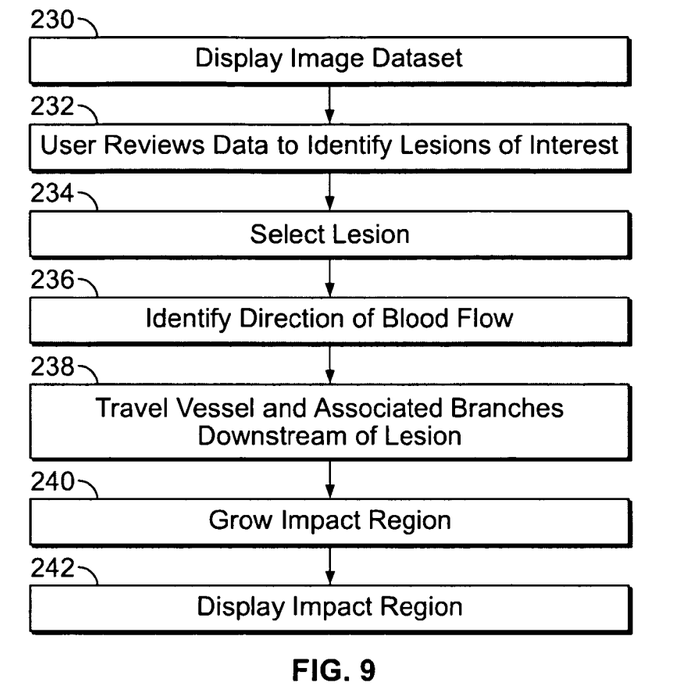
FIG. 9 illustrates a method for creating an impact atlas based on a unique patient image dataset in accordance with an embodiment of the present invention.

FIG. 9 illustrates a method for creating an impact atlas 56 based on a unique patient image dataset. This method was referred to herein above as "on-the-fly", as the impact atlas 56 is created based on the patient image data being currently operated upon. In some cases, if a patient has structural differences which are different with respect to the "normal" structures used to create a standardized anatomical atlas, the registration of the image dataset against the generalized impact atlas 56 of FIG. 3 may not be successful. In other cases, the user may not desire or need the anatomical structures labeled and/or may wish to review the patient's data without additional markings and indications. Also, some patients may have only a single or few points of interest that the user is interested in reviewing.

Figure 10:
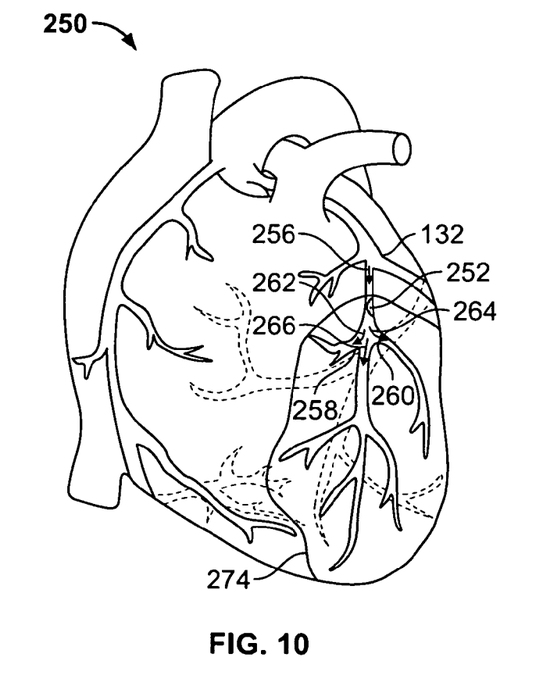
FIG. 10 illustrates an image dataset of a patient's cardiac data on the display in accordance with an embodiment of the present invention.

As in the above examples, the impact atlas 56 will be created based on the heart, although the same techniques may be applied to other anatomy, organs, structures and systems within the body. At 230, the impact atlas algorithm 54 displays a image dataset on the display 42. FIG. 10 illustrates an image dataset 250 of a patient's cardiac data on the display 42. At 232 of FIG. 9, the user reviews the image dataset 250 to identify one or more lesions of interest within the cardiac vessels. Optionally, the impact atlas algorithm 54 may automatically detect and identify lesions. At 234, the user selects a lesion 252 (FIG. 10) within a vessel with the user interface 40. In this example, the vessel is the left coronary artery 132.

At 236, the impact atlas algorithm 54 identifies the direction of blood flow within the left coronary artery 132, as indicated by arrow 256. Alternatively, the user may indicate the direction of blood flow. At 238, the impact atlas algorithm 54 travels the left coronary artery 132 and associated branches downstream of the lesion 252, in the direction of blood flow, to detect the vascular sub-network. The impact atlas algorithm 54 detects vessel branching points 258 and 260, and follows each of the branching vessels as well as continuing along the main vessel, in the direction of arrows 262, 264 and 266, respectively.

At 240 the impact atlas algorithm 54 grows an impact region 274 associated with the lesion 252 and the detected vascular sub-network. Optionally, a conceptual line may be drawn anti-distal to the lesion 252, which is treated as a boundary during region growing. The impact atlas algorithm 54 may grow the impact region 274 using one of the previously discussed region growing techniques. At 242, the impact atlas algorithm 54 displays the impact region 274 and/or other associated data.

Impact regions may also be predicted by combining aspects of the methods in FIGS. 7 and 9. For example, the user may choose to start with the method of FIG. 7, and then bring in generic data from impact atlas. Alternatively, the user may apply the method of FIG. 7 to predict the impact regions for a particular patient. In this case, collateral vessels may be present within the patient's cardiac dataset which are not present in the general anatomical atlas 58. The collateral vessels are therefore not taken into account when predicting the impact region. The user may use the on-the-fly technique of FIG. 9 to identify the collateral vessels at 238, then grow the associated impact region based on the additional anatomical information.

Impact atlas data may be displayed to the user in other formats. For example, anatomical landmarks may be presented to the user on the display. Upon selecting a desired landmark, the impact region may be displayed on a separate 3D model, bulls-eye plot, Polar Plot, or other representation.

Figure 11:
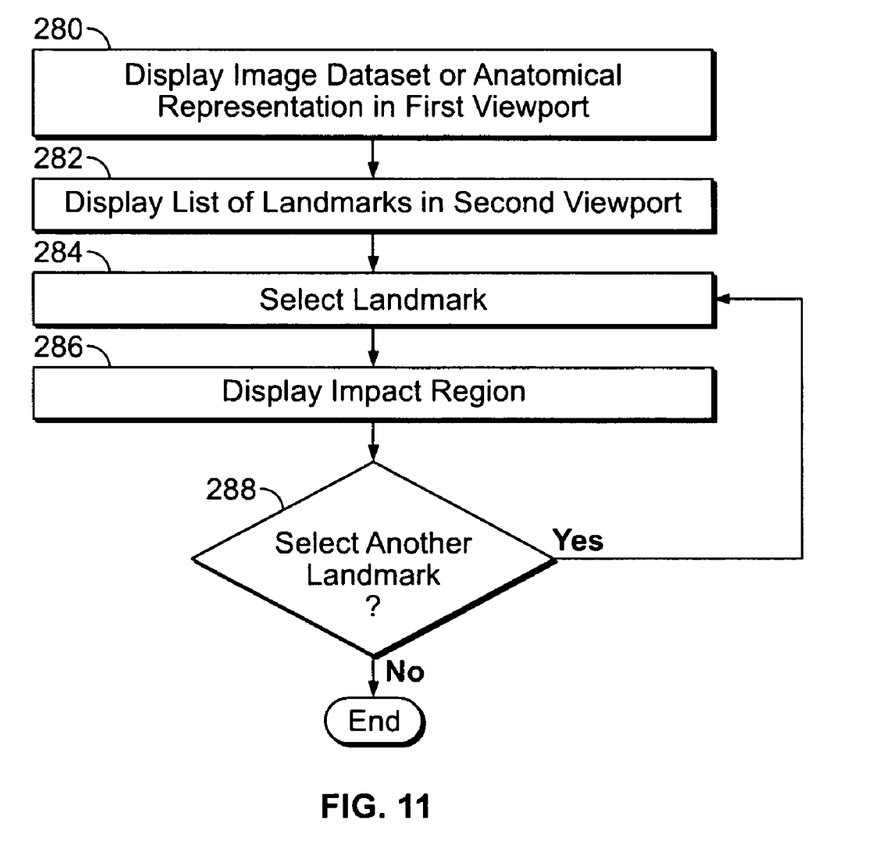
FIG. 11 illustrates a method for displaying impact region data based on selecting an anatomical point from a displayed list in accordance with an embodiment of the present invention.

FIG. 11 illustrates a method for displaying impact region data based on selecting an anatomical point from a displayed list. This method may use data from the impact atlas 56 created in FIG. 3. Within the impact atlas 56, the impact atlas algorithm 54 associates the identified vessels with the areas of functional impact. For example, a list, database, file and the like may be built and modified to maintain desired association data.

At 280, the impact atlas algorithm 54 displays the image dataset in a first viewport on the display 42. Alternatively, an image dataset of a specific patient may not be used. Instead, an anatomical representation, such as the visual representation 120 of the impact atlas 56 (FIG. 4), a line drawing, artistic representation, simplified representation and the like, may be provided.

At 282, the impact atlas algorithm 54 displays a list of landmarks in a second viewport on the display 42. Landmarks may be any predefined point or group of points within the vessels. Landmarks may also correspond to the blockage points. Optionally, the user may define a region of interest (ROI) within the image dataset, and the contents of the list may be modified to reflect only the landmarks within the ROI. Optionally, the list may display the landmarks by region of the heart, in alpha order, or other desired order.

At 284, the user selects a first landmark from the list with the user interface 40. At 286, the impact atlas algorithm 54 displays a first impact region associated with the first landmark. The impact atlas algorithm 54 may display the first impact region superimposed on the image dataset, in a third viewport on a representative model of the heart, in a bulls-eye plot, or other desired representation. The impact atlas algorithm 54 may provide textual and report representations, with or without associated graphical representation. If the user wishes to select a different or additional landmark at 288, the method returns to 284. If not, the method is complete.

Returning to 284, the user may select a second landmark from the list. A second impact region associated with the second landmark may be displayed together with the first impact region or displayed separately. Therefore, the first impact region may be removed, or the second impact region may be added to a composite display. Alternatively, the second impact region may be displayed in a fourth viewport. Additional selected landmarks may be selected and displayed in a like manner.

The techniques discussed above may be applied within a variety of application fields, such as: general diagnostic and treatment monitoring; planning, performing and monitoring surgical procedures; planning, performing and monitoring interventional radiology procedures; and planning and monitoring medical treatments. Therefore, the lesion and impact region data may be used to determine a patient's care, such as whether an invasive surgery is needed to address a lesion. The data may also be used to track the patient's progress over time. The impact atlas algorithm 54 may provide additional data to the user, such as determining a vulnerability of the plaque based on location within the heart as well as size of the deposit. Also, statistics may be computed related to the impact regions and/or for tissue within the impact regions.

A technical effect is using the impact atlas algorithm 54 and the impact atlas 56, with or without the anatomical atlas 58, to improve patient care. An impact atlas based on a large number of historical cases may be used to determine the functional impact of a blockage within a vessel, such as within the heart. Also, an impact atlas may be used which is based solely on, or partially on, a particular patient's image dataset and thus their specific anatomy and pathology. The impact atlas further accepts information from the user to more specifically tailor impact results for a particular blockage location. The results are provided visually as impact regions within an image dataset or other anatomical representation, and may also be provided in tabular, written report, or other graphical representation.

While the invention has been described in terms of various specific embodiments, those skilled in the art will recognize that the invention can be practiced with modification within the spirit and scope of the claims.

What is claimed is:

1. A method of processing a cardiac image dataset acquired from an imaging system, the method comprising:

generating a cardiac functional image dataset;
identifying coronary vasculature within the functional image dataset;
identifying a location of at least one blockage point within a first cardiac vessel, of the identified coronary vasculature;
predicting a potential blockage point based on the identified blockage point;
predicting a functional impact region based on the potential blockage point on cardiac tissue; and
providing a representation of the potential blockage point and the functional impact region.

2. The method of claim 1, wherein the predicting the functional impact is based at least partially on a cardiac anatomical atlas, the cardiac anatomical atlas being based on known historical cases.

3. The method of claim 1, wherein the predicting the functional impact is based at least partially on a cardiac impact atlas comprising functional impact regions generated using a region growing technique, the functional impact regions comprising at least a portion of the cardiac tissue.

4. The method of claim 1, further comprising:

segmenting the image dataset to identify anatomical structures comprising at least the first cardiac vessel and a portion of a vascular tree associated with the first cardiac vessel; and
growing an impact region within the image dataset based on the potential blockage point and the vascular tree, the impact region identifying at least a portion of the cardiac tissue within the image dataset experiencing decreased blood flow based on the potential blockage point, the representation being based on the impact region.

5. The method of claim 1, further comprising determining a blood flow direction within the first cardiac vessel, the functional impact being at least partially based on the blood flow direction.

6. The method of claim 1, further comprising:

registering an image dataset comprising cardiac images against a cardiac anatomical atlas, the anatomical atlas comprising at least landmarks identifying major cardiac vessels, the major cardiac vessels comprising the first cardiac vessel; and
displaying the representation of the functional impact superimposed on the image dataset.

7. The method of claim 1, wherein the functional impact is displayed in at least one of a 3D cardiac model, a 3D surface rendering of the atlas, a 3D volume rendering with marked impact regions, polar plot diagrams, textual reports, and textual summaries.

8. The method of claim 1, further comprising using a user interface to identify the potential blockage point.

9. The method of claim 1, further comprising determining a vulnerability score based on at least the location of the potential blockage point.

10. A method for creating an impact atlas for predicting impact of a potential blockage within a vessel, the method comprising:

generating a cardiac functional image dataset;
identifying coronary vasculature within the functional image dataset;
identifying a location of at least one blockage point within a first cardiac vessel of the identified coronary vasculature;
predicting potential blockage points based on the identified blockage point;
predicting a functional impact region based on the potential blockage points;

growing the predicted impact regions based on the potential blockage points within the cardiac vessels, the functional impact regions comprising at least cardiac tissue; and associating each of the blockage points with at least one of a plurality of impact regions in an impact atlas file.

11. The method of claim 10, further comprising associating physiological measures of a heart with the impact atlas file, the physiological measures comprising at least one of ejection fraction, stroke volume, blood flow direction, flow pressure, and heart wall movement.

12. The method of claim 10, further comprising:
identifying a location of a lesion within a second image dataset having diagnostic image data associated with a patient; and
identifying at least one of the blockage points and at least one associated impact region corresponding to a potential impact within the second image dataset based on at least the location of the lesion.

13. The method of claim 10, further comprising:
identifying a location of a lesion within a second image dataset having diagnostic image data associated with a patient;
identifying at least one of the blockage points or at least one of the associated impact regions, based on the location of the lesion; and
displaying a functional impact of the lesion based on at least one of the associated impact regions.

14. The method of claim 10, further comprising:
identifying a location of a lesion within a second image dataset having diagnostic image data associated with a patient;
identifying at least one of the blockage points and at least one associated impact region based on at least the location of the lesion; and
creating a report representative of a functional impact of the lesion based on at least the at least one associated impact region, the report comprising at least one of a textual format and a graphical format.

15. A system for displaying potential impact of an occlusion within a coronary vessel, comprising:
a display for displaying an image dataset comprising at least anatomical structures indicative of cardiac vessels and a list of anatomical points identifying locations within the cardiac vessels, each of the anatomical points having at least one associated potential impact region defining an area of decreased blood flow based on an occlusion located proximate to the anatomical point;
a user interface for selecting at least one anatomical point from the list based on at least a potential occlusion point;
a processor coupled to the display and the user interface, the processor configured to identify data associated with the anatomical point, the display displaying the data representative of the potential impact region associated with the anatomical point;
the processor configured to: generate a cardiac functional image dataset;
identify coronary vasculature within the functional image dataset;
locate at least one blockage point within a first cardiac vessel of the identified coronary vasculature;
predict a potential blockage point based on the identified blockage point, and a functional impact region based on the potential blockage point on cardiac tissue.

16. The system of claim 15, wherein the image dataset further comprises diagnostic image data of a patient, the user interface identifying a lesion within the image dataset, the potential occlusion point being based on a location of the lesion.

17. The system of claim 15, the display further displaying the data representative of the potential impact region as one of separate from the image dataset and superimposed on the image dataset.

18. The system of claim 15, the display further displaying the data representative of the potential impact region separate from the image dataset, the data comprising at least one of a visual region superimposed on a model representing at least one of a heart, a text based display, or a report.

19. The system of claim 15, further comprising:
the user interface selecting a second anatomical point from the list based on a second potential occlusion point identified based on the image dataset;
the processor identifying data associated with the second anatomical point; and
the display displaying the data representative of at least one of the potential impact regions associated with at least one of the anatomical points separate from the image dataset, the data comprising at least one of the impact regions superimposed on at least one model representative of a heart, a textual display, and a report.

20. The system of claim 15, further comprising:
at least one of the user interface and the processor defining a percentage of occlusion associated with the potential occlusion point; and
the processor modifying the display of the data based on the percentage of occlusion.

* * * * *